United States Patent
Rosenberg et al.

(10) Patent No.: US 7,931,567 B2
(45) Date of Patent: Apr. 26, 2011

(54) APPARATUS FOR ISOLATING AN INJURED ANKLE OR FOOT DURING AEROBIC EXERCISE

(76) Inventors: Leon Rosenberg, Cherry Hill, NJ (US); Stephen Cohen, Cherry Hill, NJ (US)

( * ) Notice: Subject to any disclaimer, the term of this patent is extended or adjusted under 35 U.S.C. 154(b) by 146 days.

(21) Appl. No.: 12/399,623

(22) Filed: Mar. 6, 2009

(65) Prior Publication Data

US 2010/0227741 A1   Sep. 9, 2010

(51) Int. Cl.
*A63B 69/16* (2006.01)
*A61F 5/01* (2006.01)

(52) U.S. Cl. .............................. 482/57; 602/16; 600/587

(58) Field of Classification Search .................... 482/51, 482/57–63, 79–80; 601/33–35, 23, 5; 602/16, 602/27; 600/587
See application file for complete search history.

(56) References Cited

U.S. PATENT DOCUMENTS

| | | | |
|---|---|---|---|
| 2,439,100 A * | 4/1948 | Richards | 602/28 |
| 4,306,714 A | 12/1981 | Loomis et al. | |
| 4,371,161 A | 2/1983 | Williams | |
| 4,432,543 A | 2/1984 | Normandin | |
| 4,718,665 A * | 1/1988 | Airy et al. | 482/119 |
| 4,733,859 A | 3/1988 | Kock | |
| 4,795,148 A * | 1/1989 | Rangaswamy | 482/80 |
| 4,817,588 A * | 4/1989 | Bledsoe | 602/16 |
| 4,856,500 A * | 8/1989 | Spademan | 602/26 |
| 5,052,379 A * | 10/1991 | Airy et al. | 602/16 |
| 5,144,943 A * | 9/1992 | Luttrell et al. | 601/34 |
| 5,215,508 A | 6/1993 | Bastow | |
| 5,344,390 A | 9/1994 | Motloch | |
| 5,352,185 A | 10/1994 | Blauth | |
| 5,851,166 A | 12/1998 | Bernardson | |
| 5,980,435 A * | 11/1999 | Joutras et al. | 482/114 |
| 6,053,853 A | 4/2000 | Hinds | |
| 6,142,914 A | 11/2000 | Crawford et al. | |
| 6,217,488 B1 | 4/2001 | Bernardson | |
| 6,471,664 B1 | 10/2002 | Campbell et al. | |
| D496,106 S * | 9/2004 | Iglesias et al. | D24/190 |
| 6,834,752 B2 * | 12/2004 | Irby et al. | 192/81 C |
| 6,872,187 B1 * | 3/2005 | Stark et al. | 602/16 |
| 7,192,410 B1 | 3/2007 | Rodgers | |
| 7,297,091 B2 | 11/2007 | Nushart | |
| 7,354,384 B2 | 4/2008 | Martin et al. | |
| 7,416,537 B1 * | 8/2008 | Stark et al. | 602/16 |
| 2002/0193210 A1 | 12/2002 | Turner | |
| 2008/0015091 A1 | 1/2008 | Tyree | |

* cited by examiner

*Primary Examiner* — Steve R Crow

(74) *Attorney, Agent, or Firm* — Michael B. Fein; Cozen O'Connor

(57) ABSTRACT

An exercise apparatus and method for isolating an ankle during aerobic exercise on a bicycle configured to be worn on the leg of a person having an ankle injury so that the person may operate the bicycle with the leg having the ankle injury without pressure on the ankle, wherein weight and force are distributed from the pedal to the calf and thigh without implicating the ankle.

12 Claims, 4 Drawing Sheets

APPARATUS FOR ISOLATING AN INJURED ANKLE OR FOOT DURING AEROBIC EXERCISE

BACKGROUND OF THE INVENTION

The present invention relates an orthopedic device and method of use. More particularly, the invention relates to a system and method for isolating an injured ankle or foot during aerobic exercise.

Many exercise devices of various types have been proposed and used, some of which being directed to specific body parts such as legs, arms, knees, feet, fingers, or toes.

For example, U.S. Pat. No. 4,306,714 to Loomis, et al. discloses an exercise device for the hands or feet in which the user supplies the force and motion by one hand or foot which will be countered by a resistance and similar motion of the other hand or foot.

U.S. Pat. No. 4,432,543 to Normandin, discloses a physiotherapeutic self-exerciser which enables a patient to apply traction to the muscles or tendons of the feet whereby the patient may exert the necessary tension which is required to exercise a tendon or muscle to be treated. The exerciser includes a sabot (similar to a sandal or shoe having a band of leather or other material across the instep) to which the patient's foot is attached and a pair of levers which are manually engageable by the patient. The patient gradually applies weight to the levers connected to the sabot, thereby exerting an upward tension of the sabot, and the latter, combined with the flexing of the patient's knee, exerts a predetermined traction on the tendon or muscle to be treated.

Nushart, U.S. Pat. No. 7,297,091, discloses an apparatus and method of use designed to prepare a previously injured ankle joint for the strengthening exercises inherent in the physical medicine/rehabilitation process by reducing pain and stiffness and increasing flexibility and range of motion, wherein a patient's foot is secured in an apparatus and an Ankle Mortise Strap is looped around the mortise of an ankle of the foot. A force strap is attached to the ends of the Ankle Mortise Strap. Anterior mobilization is achieved by moving the force strap ventrally from the foot so that the foot including the talus remains stationary while the tibia and fibula glide anteriorly. Posterior mobilizations are achieved by securing the foot, and looping an Ankle Mortise Strap around the front of the ankle.

Bernardson, U.S. Pat. No. 6,217,488, discloses a rocking-type foot and lower leg exercising apparatus incorporates one or two centrally pivoted pedals mounted upon a base in a position facilitating the placement of the feet of the user upon such pedal or pedals while seated in a chair and rocking of the pedals with the foot positioned upon them to provide a soothing motion that will maintain the tone of the muscles of the legs and encourages blood circulation in the feet and legs. The pivot point of the pedal or pedals may be located at any vertical position between the base and the pedal, but is located longitudinally, between about one fourth to one half of the distance from the end of the pedal or pedals. A motor, solenoid, actuator, or other electrical hydraulic or pneumatic means or any combination thereof may be provided to generate rocking-type motion of the pedals.

Crawford, et al., U.S. Pat. No. 6,142,914, discloses an exercise device is provided for removable attachment to the foot rests of a wheelchair to enable a person sitting in the seat of the wheelchair to exercise at least one of his or her arms and legs. The device includes a base slidably received on the foot rests and an exercising arrangement adjustably mounted on the base to accommodate the physical stature of a person sitting in the wheelchair.

Hinds, U.S. Pat. No. 6,053,853, discloses an exercise wheel comprising means for emplacement of an operator's feet whereby he or she orients the body such that the hands are rigidly placed against the underlying surface and the wheel is alternately projected and retracted so as to exercise certain muscles.

Bernardson, U.S. Pat. No. 5,851,166 discloses a lower extremity exercise apparatus adapted for facilitating movement of the feet and lower legs of a seated person comprising a rocking-type foot and lower leg exercising apparatus incorporates one or two centrally pivoted pedals mounted upon a base in a position facilitating the placement of the feet of the user upon such pedals while seated in a chair and rocking of the pedals with the foot positioned upon them to provide a soothing motion that will maintain the tone of the muscles of the legs and encourages blood circulation in the feet and legs. The pivot point of the pedals may be located at any vertical position between the base and the pedal, but is located longitudinally between about one fourth to one half of the distance from the end of the heel position on the pedals.

Tyree, U.S. Pat. Publ. 2008/0015091, discloses exercise machines for the leg muscles using separate machines for the biceps femoris and quadriceps and with the biceps femoris machines configured so that the muscle attachment below the knee is the "origin" and muscle attachment of the upper leg and hip bone is the "insertion".

Martin U.S. Pat. No. 7,354,384, discloses an exercise apparatus and method for permitting a wheelchair occupant to perform a variety of exercises without the need to leave a seated position. First and second foot assemblies are each configured to receive a respective foot of a seated user of the apparatus. The first and second foot assemblies are mounted on the support base to permit selective performance and switching between a pivoting exercise and a translational sliding exercise.

Motloch U.S. Pat. No. 5,344,390 discloses an orthopedic device which includes connected modules beginning with a knee module which facilitates an impaired individual's ability to stand or walk by alignment of the upper porting of the individual's leg with the lower portion of that leg.

Ankle and foot exercising devices are also disclosed in U.S. Pat. Nos. 5,352,185, 4,371,161, 4,733,859, 5,215,508, 7,192,410, 6,471,664, and published application US2002/0193210.

However, no device has been disclosed or used for the specific purpose of isolating an injured an ankle or foot during aerobic exercise, or for facilitating exercise on a bicycle or stationary bicycle by a person who has an ankle or foot injury. Ankle and foot injuries are usually treated by rigid or flexible casting and the use of crutches, but even with rigid casts it is important not to put significant weight on the bottom of the cast or to apply significant force to the cast. In the case of flexible casts, it is especially important not to place weight or force on the foot. Because of the need to avoid weight, force, or pressure on the foot having the ankle or foot injury, exercise is limited, especially exercise which involves the leg and foot having the ankle injury. For individuals who wish to exercise when one of their ankles is injured, no prior device or apparatus is designed to facilitate such exercise.

It is an object of the present invention to facilitate exercise by individuals who suffer from an injury of an ankle or foot. It is another object to facilitate aerobic exercise by such individuals while protecting an injured ankle or foot from force, stress, pressure, and weight. Another object is to facilitate such exercise on a stationary bicycle.

SUMMARY OF THE INVENTION

These objects, and others which will become apparent from the following description and drawings, are achieved by the present invention which comprises in one aspect an apparatus and method for isolating an ankle or foot during exercise on a bicycle or stationary bicycle having pedals attached to crankshafts configured to be worn on the leg of a person having the injury so that the person may operate the bicycle or stationary bicycle with the leg having the ankle and/or foot injury without pressure on the ankle or foot, wherein weight and force are distributed from a pedal to the calf and thigh without implicating the ankle or foot.

In another aspect, the invention comprises an exercise apparatus for isolating an ankle or foot during aerobic exercise on a bicycle or stationary bicycle comprising a thigh cuff, a calf cuff, a bottom plate, an outer hinge joint, an inner hinge joint, a pedal retention member configured to secure the bottom plate to a pedal of a bicycle or stationary bicycle, at least one rigid member connecting the thigh cuff to the outer and inner hinge joints, at least one rigid member connecting the calf cuff and the bottom plate to the hinge joints, the apparatus configured to be worn on the leg of a person having an ankle injury so that when the bottom plate is secured to a pedal, the person may operate the bicycle or stationary bicycle without pressure on the injured ankle and/or foot, wherein weight and force are distributed from the pedal to the calf and thigh without implicating the ankle or foot. If both the ankle and foot are injured, the invention functions to isolate both during aerobic exercise.

In some embodiments an inner thigh bar connects the thigh cuff to the inner hinge joint, an outer thigh bar connecting the thigh cuff to the outer hinge joint, an inner calf bar connects the calf cuff to the inner hinge joint, an outer calf bar connects the calf cuff to the outer hinge joint, and the inner and outer calf bars are connected to the inside and outside of bottom plate, respectively.

In other embodiments the hinge joints are connected to the thigh cuff with a rigid plastic member, and a second rigid plastic member connects the hinge joints to the calf cuff. The second rigid plastic member can also connect the hinge joints and calf cuffs to the bottom plate or, alternatively, a third rigid member can connect the calf cuff to the bottom plate.

In certain embodiments the distance between the bottom plate and the hinge joints is adjustable so that the bottom plate would not exert force on the bottom of the individual's foot during use on a bicycle or stationary bicycle. It is preferable to have a space between the bottom plate and the bottom of the foot, although in some embodiments the bottom plate can be in contact with the bottom of the individual's foot during use, as long as most of the force is transferred from the pedal to the plate to the calf cuff, through the hinges, and to thigh cuff. In most embodiments the individual is actually pedaling the bicycle with the calf and thigh rather than with the foot of the leg (or legs) which suffers from the ankle injury (or injuries).

Various ways of securing the thigh cuff to the thighs, calf cuff to the calf, and bottom plate to the pedal are possible, including, for example, "Velcro" fabric or clips which are either metal, composite, plastic, or any other rigid material.

In embodiments which include an inner and outer calf and thigh bars, the bars can be any material, for example plastic, composite, metal, or any other rigid material.

In operation, the individual having one or more injured ankles can use the apparatus to enable exercising on a bicycle having pedals by securing the thigh cuff to the thigh, securing the calf cuff to the calf while arranging the apparatus so that the hinge joints are adjacent to each side of the individual's knee, securing the bottom plate to a pedal by securing the pedal retention member to the pedal, and operating the bicycle by pedaling in a normal manner. Use of the apparatus in this way isolates the injured ankle from the force of the pedal and such force is redistributed to the thigh and the calf of the leg which has the ankle injury.

By "stationary bicycle" is meant any exercise machine having pedals which remains in one location, for example machines known as upright stationary bicycles, recombinant stationary bicycles, exercycles, stationary bicycles, and cycles can be used with the apparatus and method of the invention. As mentioned, the device can also be used with a regular bicycle.

The apparatus can be worn around a cast, around a boot, attached to a knee brace, built into a cast, built into a knee brace, built into a boot or shoe, or any other suitable configuration which does not interfere with the intended purpose of the apparatus and method.

When the apparatus causes an imbalance due to the extra distance being added between the bottom of the injured foot and a pedal, a block for the other pedal, i.e., the pedal being used by the non-injured foot, can be employed to even out the length. In embodiments which include such a block for the other pedal, toe straps can be used to secure the block to the pedal or to secure the uninjured foot to the pedal through the block. The invention can be in the form of a kit which includes the orthopedic apparatus and the block wherein the block is configured to be attached to a pedal and compensate for added distance between the bottom of the injured foot and the pedal to which the bottom plate of the apparatus is secured.

The apparatus can be attached to a standard pedal or quick release pedal, or any other pedal which allows the user to turn the crank shaft of the stationary bicycle.

In an alternative embodiment, the apparatus can be attached directly to the crank shaft of the stationary bicycle after removing a pedal, i.e., it is not necessary to secure the apparatus to a pedal; the bottom plate or other member of the apparatus can include a screw of the same size as the pedal which has been removed, in which case the screw on the bottom plate can be inserted into the crankshaft after the pedal is removed. Alternatively, a separate device can be screwed into the threaded pedal opening in the crankshaft and the bottom plate can have a connector to mate with such separate device.

The device can include an anti-skid pad on the bottom plate or any other location to prevent the individual's foot from slipping off of the device during exercise.

The apparatus can be used not only for individual's with ankle injuries, but can also be used by individuals with injuries to a foot or upper or lower leg. It is not presently contemplated that the apparatus can be used by individuals with knee injuries.

The apparatus is especially useful for individuals who are accustomed to exercise for whom absence of ability to exercise when recovering from an ankle, foot, or leg injury is a serious problem or inconvenience.

DETAILED DESCRIPTION

Figure 1:
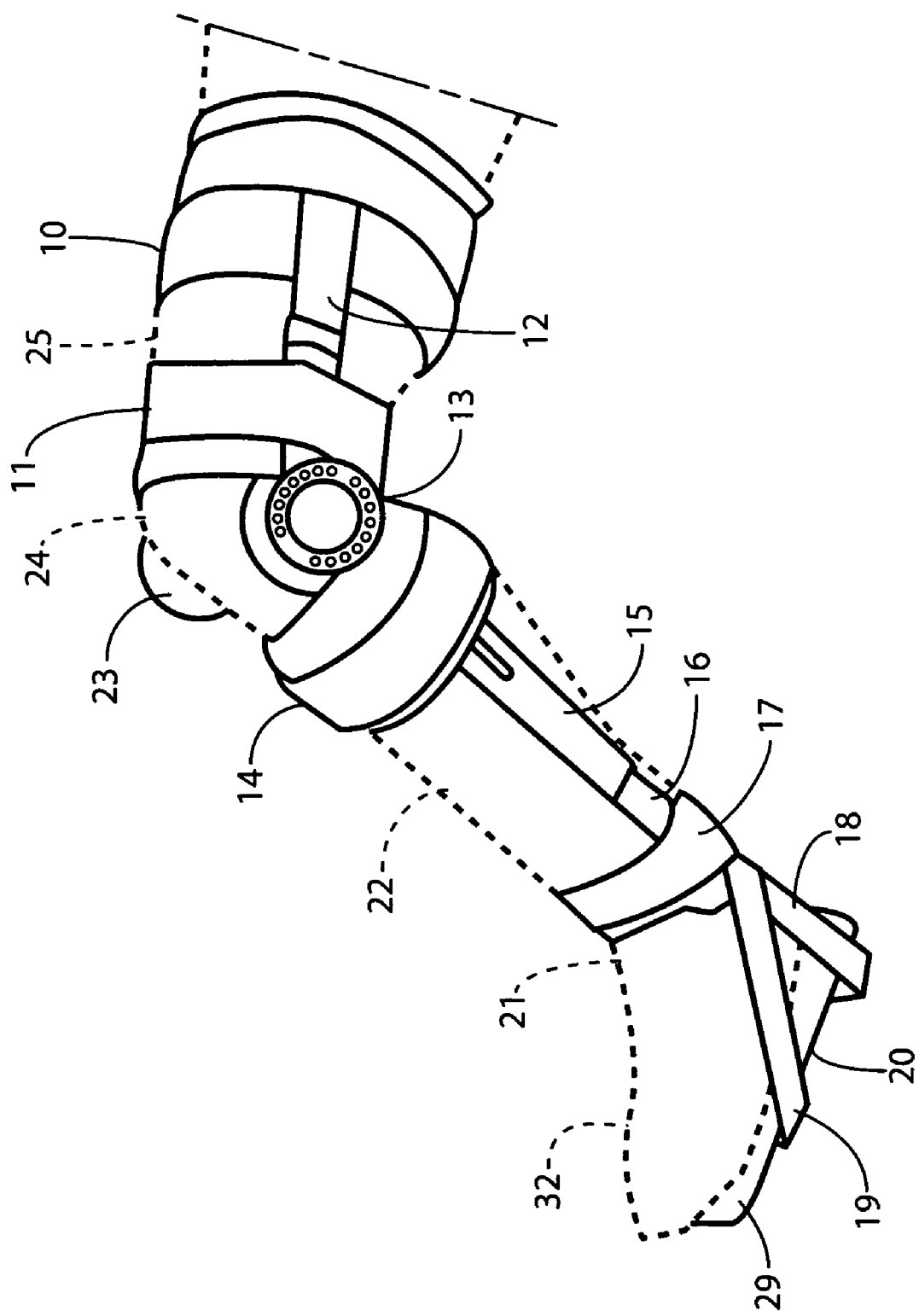
FIG. 1 is a side perspective view of an apparatus according to the invention being worn on an individual's leg.
Figure 2:
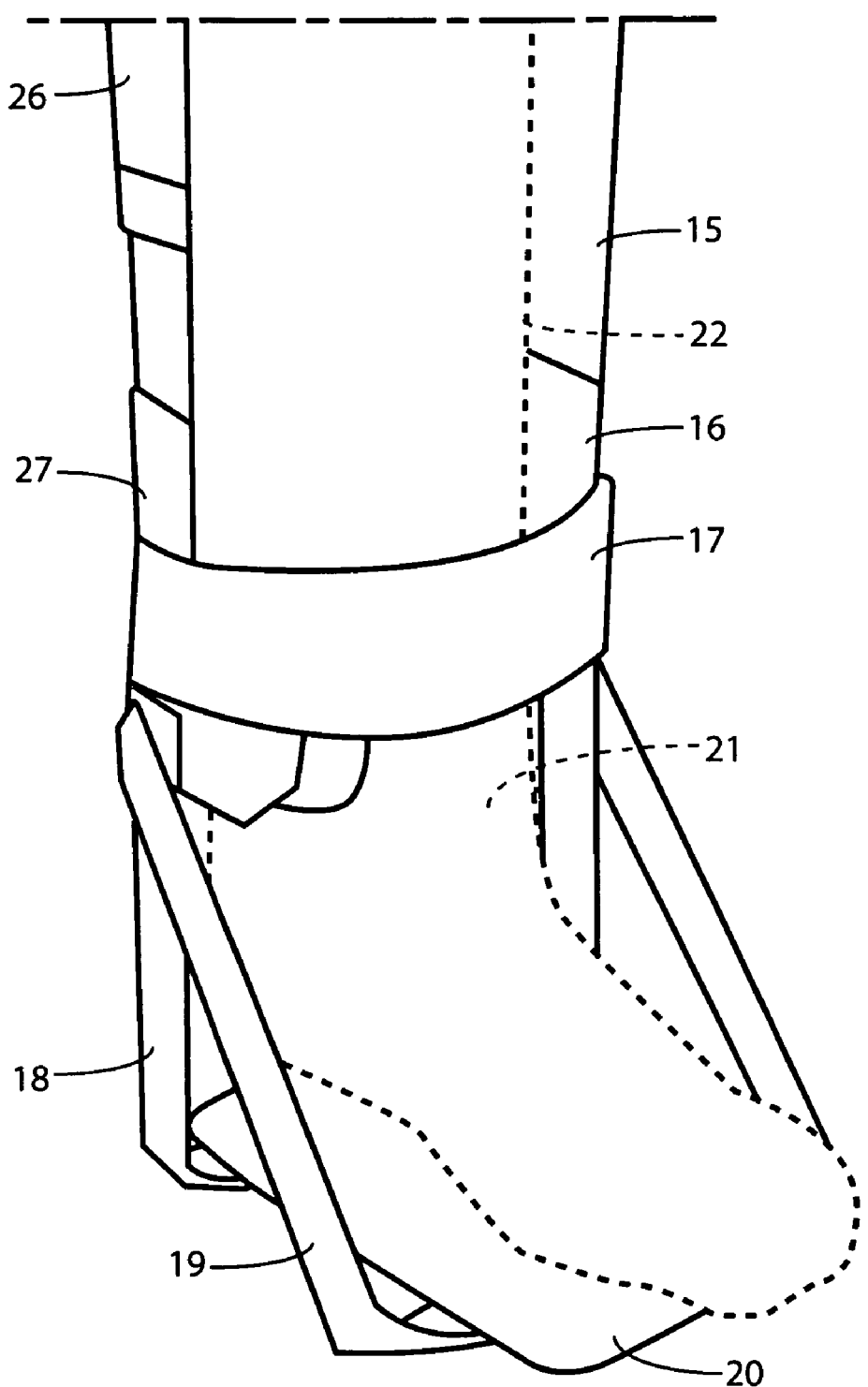
FIG. 2 is a front perspective view of the bottom portion of an apparatus according to the invention illustrating the separation between the bottom plate and the bottom of the foot.
Figure 3:
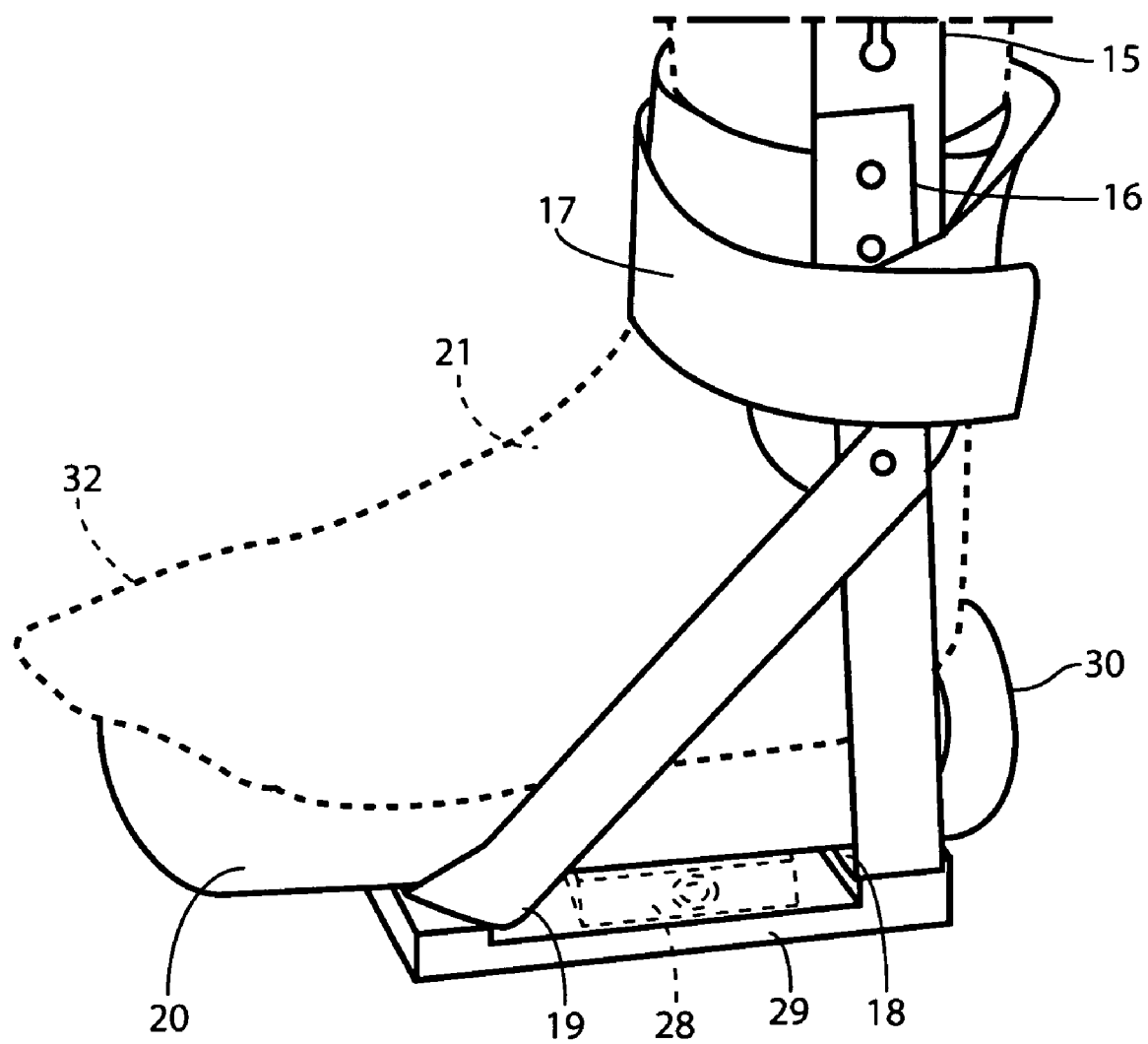
FIG. 3 is a side view of the bottom portion of apparatus of the invention being worn by an individual with a foot located above the bottom plate, illustrating an embodiment with a removable pedal brace member attached to the bottom plate with a pedal being secured by a clamp at the rear of the apparatus.

Referring to the figures generally and in particular to FIGS. 1-3, in FIG. 1 an embodiment of an apparatus according to the invention is shown on an individual's leg having a thigh 25, calf 22, ankle 21, and foot 32, the leg of course not forming part of the invention. The illustrated embodiment includes an upper thigh cuff 10 secured to the individual's thigh 25 and to upper outer thigh bar 12, which is connected to outer hinge 13. In the illustrated embodiment a lower thigh cuff 11 is wrapped around and secured to the thigh bar 12. Upper calf cuff 14 secures the first section of outer calf bar 15 to the calf 22, the first section 15 of the outer calf bar mechanically joining the outer hinge 13 to the second, lower section 16 of outer calf bar which is secured to the lower portion of the calf 22 by lower calf cuff 17. The lower section 16 of the outer calf bar continues to lower U-shaped member 18 which continues horizontally and then back vertically on the inside to a lower section of an inner calf bar (27 in FIG. 2). Lower section 16, lower U-shaped member 18, and inner calf bar 27 can be a single formed section of plastic, composite, metal, or any other rigid material. The inner hinge 23 is shown opposite the outer hinge 13, with the individual's knee 24 between the inner hinge 23 and outer hinge 13. The individual's thigh 25 is shown with the upper 10 and lower 11 thigh cuffs secured thereto.

A forward U-shaped support member 19 joins lower U-shaped member 18 and lower plate 20 and supports the front side of the lower plate 20. The lower U-shaped member 18 supports the back of the lower plate 20. The individual's injured ankle 21 is protected from force and weight by U-shaped members 18 and 19 and plate 20. The plate 20 can also be a pad, or can be a plate covered by a pad. The plate or pad 20 acts to protect the bottom of the foot 32 from contact with a pedal 28 (FIG. 3), and the apparatus should be worn so that there is a space or gap between the bottom of the foot 32 and the top of pad 20.

Referring now to FIG. 2, the individual's calf 22 is between the first section of outer calf bar 15, corresponding first section of inner calf bar 26, lower section of outer calf bar 16 and lower section of inner calf bar 27, and lower calf cuff 17. Ankle 21 and foot 32 are isolated from pad 20 which in turn comes in contact with a pedal of an exercise machine such as a stationary bicycle. The pad 20 is supported by forward U-shaped support member 19 and bottom U-shaped support member 18. Force is transferred from the pad 20 to U-shaped support members 18 and 19, then to lower section 27 of inner calf bar on to first section 26 of inner calf bar, and to lower section 16 of outer calf bar on to first section 15 of outer calf bar. Referring to FIG. 1 again, the force is transferred further to outer hinge 13, inner hinge 23, outer thigh bar 12 and the inner thigh bar (not shown), and then on to the thigh 25 and calf 22 via upper thigh cuff 10, lower thigh cuff 11, upper calf cuff 14, and lower calf cuff 17.

Referring now to FIG. 3, pedal 28 is shown being secured in one embodiment by pedal retention member 29, which is one embodiment of such a member configured to secure the bottom plate to a pedal 29 of a stationary bicycle with clip 30. The pedal retention member 29 is hinged to front U-shaped member 19 so that when clip 30 is moved to release the rear side of the pedal retention member 29, the pedal 28 is easily released from below the pad 20.

Figure 4:
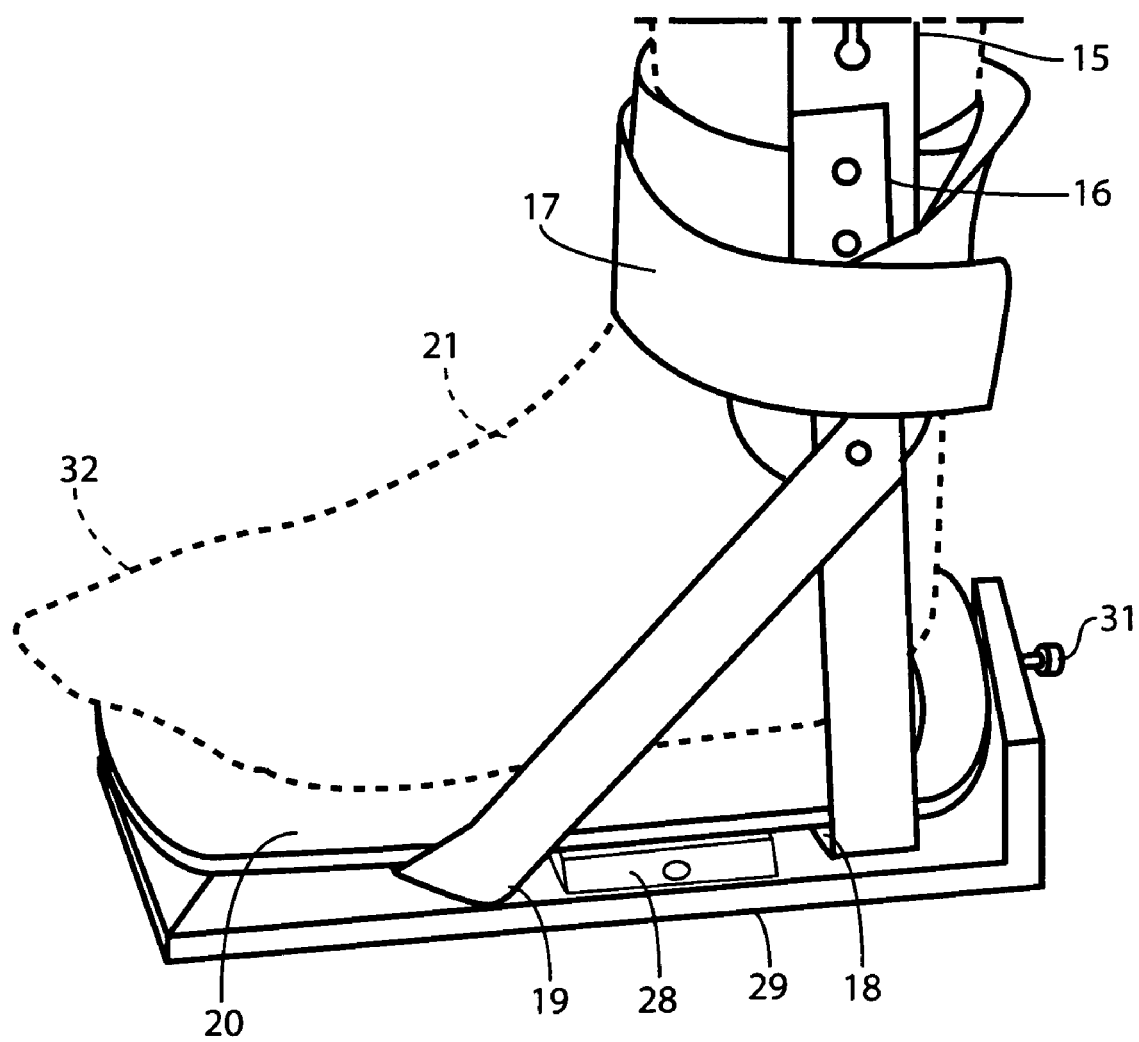
FIG. 4 is a side view of the bottom portion of the apparatus as in FIG. 3 except that the bottom plate is secured by a thumb screw.

Referring to FIG. 4, a second embodiment of a system to secure the pedal retention member 29 to the rear of the pad 20 is illustrated wherein a thumb screw 31 retains the pedal retention member 29 in place to secure the pedal 28 during exercise, and is then released by unscrewing the thumb screw 39 when exercise is completed.

In general, the figures illustrate an apparatus for use by an individual with an ankle or foot injury exercising on a stationary bicycle having pedals by a method which comprises securing an upper thigh cuff 10, or thigh cuffs 10 and 11, to the individual's thigh 25, securing a calf cuff 14 or two calf cuffs 14 and 17 to the individual's calf 22 while arranging the apparatus so that the hinge joints 13, 23 are adjacent to each side of the individual's knee 24, optionally securing a bottom plate 20 to a pedal 28 by securing the pedal retention member 29 to the pedal 28, and operating the stationary bicycle by pedaling in a normal manner, wherein the ankle 21 and foot 32 of the individual are isolated from the force of the pedal 28 and such force is redistributed to the thigh 25 and the calf 22.

The present invention, therefore, is well adapted to carry out the objects and attain the ends and advantages mentioned, as well as others inherent therein. While the invention has been depicted and described and is defined by reference to particular preferred embodiments of the invention, such references do not imply a limitation on the invention, and no such limitation is to be inferred. The invention is capable of considerable modification, alteration and equivalents in form and function, as will occur to those ordinarily skilled in the pertinent arts. The depicted and described preferred embodiments of the invention are exemplary only and are not exhaustive of the scope of the invention. Consequently, the invention is intended to be limited only by the spirit and scope of the appended claims, giving full cognizance to equivalents in all respects.

What is claimed is:

1. An exercise apparatus for isolating an ankle during aerobic exercise on a bicycle comprising a thigh cuff, a calf cuff, a bottom plate, an outer hinge joint, an inner hinge joint, a pedal or crankshaft retention member configured to secure the bottom plate to a pedal or crankshaft of a bicycle, at least one rigid member connecting the thigh cuff to the outer and inner hinge joints, at least one rigid member connecting the calf cuff and the bottom plate to the hinge joints, the apparatus configured to be worn on the leg of a person having an ankle injury so that when the bottom plate is secured to a pedal or crankshaft, the person may operate the bicycle with the leg having the ankle injury without pressure on the ankle, wherein weight and force are distributed from the pedal to the calf and thigh without implicating the ankle;

wherein said retention member is the only interconnection between said bottom plate and the pedal or crankshaft, such that no forces are exerted on the bottom of the user's foot during operation of the bicycle.

2. The exercise apparatus of claim 1 wherein the at least one rigid member connecting the thigh cuff to the outer and inner hinge joints comprise an inner thigh bar connecting the thigh cuff to the inner hinge joint and an outer thigh bar connecting the thigh cuff to the outer hinge joint, and wherein the at least one rigid member connecting the calf cuff and the bottom plate to the hinge joints comprise an inner calf bar connecting the calf cuff to the inner hinge joint, an outer calf bar connecting the calf cuff to the outer hinge joint, the inner calf bar connected to the inside of bottom plate, the outer calf bar connected to the outside of the bottom plate.

3. The apparatus of claim 2 wherein the inner calf bar, outer calf bar, inner thigh bar, and outer thigh bar are composite, carbon fiber, metal, plastic, or a combination thereof.

4. The apparatus of claim 2 wherein the inner hinge joint and outer hinge joint are metal and the bottom plate is composite, carbon fiber, metal, plastic, or a combination thereof.

5. The apparatus of claim 2 wherein the inner calf bar and outer calf bar have means to adjust the length so that the bottom plate does not exert force on the bottom of the user's foot during operation of the bicycle.

6. The exercise apparatus of claim 1 wherein the at least one rigid member connecting the thigh cuff to the outer and inner hinge joints comprises a first plastic molding connecting the thigh cuff to the inner hinge joint, and wherein the at least one rigid member connecting the calf cuff and the bottom plate to the hinge joints comprise a second plastic molding connecting the calf cuff to the inner and outer hinge joints, and the bottom plate.

7. The apparatus of claim 1 wherein the thigh cuff and calf cuff are comprised of Velcro straps.

8. The apparatus of claim 1 wherein the means for securing the bottom plate to the pedal is comprised of a Velcro strap.

9. The apparatus of claim 1 wherein the pedal or crankshaft retention member configured to secure the bottom plate to a pedal or crankshaft of a bicycle comprises a metal or plastic clip secured to the bottom of the bottom plate.

10. The apparatus of claim 1 wherein the pedal or crankshaft retention member configured to secure the bottom plate to a pedal or crankshaft of a bicycle comprises a screw extending horizontally from the bottom plate having the same threading and diameter as a pedal screw, the screw configured to mate with a hole on a crankshaft.

11. A kit comprising the apparatus of claim 1 and a block configured to be attached to a pedal and compensate for added distance between the bottom of the injured foot and the pedal to which the bottom plate of the apparatus is secured.

12. A method of exercising on a bicycle having pedals by an individual comprising providing an apparatus according to claim 1, securing the thigh cuff to the individual's thigh, securing the calf cuff to the individual's calf while arranging the apparatus so that the hinge joints are adjacent to each side of the individual's knee, securing the bottom plate to a pedal or a crankshaft by securing the pedal retention member to the pedal or crankshaft, and operating the bicycle by pedaling in a normal manner, wherein the ankle of the individual is isolated from the force of the pedal and such force is redistributed to the thigh and the calf.

* * * * *